United States Patent [19]

Nugent et al.

[11] Patent Number: 4,555,336

[45] Date of Patent: * Nov. 26, 1985

[54] POUR SPOUT FOR CONTAINER WITH IMPROVED POURING FEATURE

[75] Inventors: Edward L. Nugent, North Caldwell; Lawrence Lutkowski, East Rutherford, both of N.J.

[73] Assignee: Becton, Dickinson and Company, Paramus, N.J.

[*] Notice: The portion of the term of this patent subsequent to Nov. 26, 2002 has been disclaimed.

[21] Appl. No.: 176,932

[22] Filed: Aug. 11, 1980

[51] Int. Cl.⁴ ............................................. B01D 35/02
[52] U.S. Cl. ..................................... 210/232; 210/359; 210/469; 210/472; 222/189
[58] Field of Search ............... 210/466, 467, 468, 469, 210/359, 927, DIG. 24, 472, 232; 137/801; 222/570, 567, 189, 188; 220/367

[56] References Cited

U.S. PATENT DOCUMENTS

| | | | |
|---|---|---|---|
| 2,645,382 | 7/1953 | Plough | 210/359 X |
| 3,852,194 | 12/1974 | Zine, Jr. | 210/83 |
| 3,951,798 | 4/1976 | Haldopoulos | 210/927 X |
| 4,131,549 | 12/1978 | Ferrara | 210/359 |

*Primary Examiner*—Frank Spear
*Attorney, Agent, or Firm*—Richard J. Rodrick

[57] ABSTRACT

A pouring spout for a container, particularly for decantation by pouring, of a liquid phase from the container and formed with a fluid passageway having a screen angularly disposed therein for the removal of solids from the liquid being poured from the container. A vent is provided in the pouring spout to facilitate pressure equalization to minimize or eliminate ebullition.

17 Claims, 5 Drawing Figures

POUR SPOUT FOR CONTAINER WITH IMPROVED POURING FEATURE

BACKGROUND OF THE INVENTION

This invention relates to a cap for a container, and more particularly to a novel pouring spout to facilitate the withdrawal of a liquid from a container, such as a body fluid from a test tube and the like.

Evacuated tubes are routinely used for the collection of blood specimens and transportation to laboratory for analysis. Much analysis involves the separation of blood into its light and heavy phases by centrifugation. Simple collection procedure requires that the serum be promptly transferred to another tube to prevent the continuing interaction of the blood components.

Serum separation tubes such as described in U.S. Pat. No. 3,852,194 to A. R. Zine, Jr., achieve prompt separation of the blood components by means of a barrier material which is brought into place between the blood phases during centrifugation. This permits the liquid phase to be stored in the orginal container with the obvious benefits in cost and sample identification. Since the stopper is generally discarded when the first sample is aliquoted, the tube will often remain uncovered until the final sample is taken and the tube covered for long term storage.

In order to aliquot uncontaminated specimens without spillage, a number of transfer devices are frequently used such as pipettes and filter devices. It is important that pipettes be discarded immediately after use to prevent cross contamination with another specimen. Depending on the particular procedures used in the laboratory, this will often result in the use of more than one pipette.

Conversely, use of tubes with barrier materials permits storage on the barrier without the necessity of decanting the serum.

OBJECT OF THE INVENTION

It is an object of the present invention to provide a novel pouring spout for a container, such as a tubular container to direct and for the control flow of a liquid from such a container.

Still another object of the present invention is to provide a novel pouring spout for a container and having a screen means for the removal of solids from the liquid being withdrawn from such container.

A further object of the present invention is to provide a novel pouring spout for a container as an alternative to known transfer devices, particularly for handling body fluids.

Still another object of the present invention is to provide a novel pouring spout for a container, which permits of long term storage of a liquid sample in an original collection container.

A still further object of the present invention is to provide a novel pouring spout for a container, such as a test tube, which permits of one time usage.

SUMMARY OF THE INVENTION

These and other objects of the present invention are achieved by a novel pouring spout for a container, such as a tubular container and formed with a fluid passageway having a screen means disposed therein for the removal of solids (such as fibrin from blood) from the liquid being withdrawn from the container. A channel is provided in the pouring spout to facilitate pressure equalization to minimize or eliminate ebullition, which would result if pressure equalization is effected by air passing in countercurrent flow to the liquid flowing through the fluid passageway.

DETAILED DESCRIPTION

Figure 1:
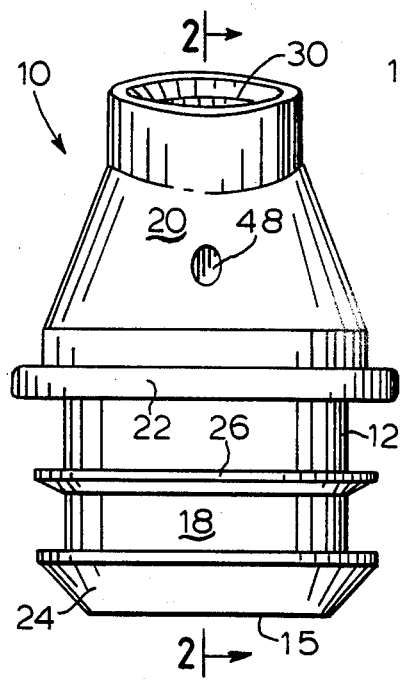
FIG. 1 is an elevational front view of the present invention.
Figure 2:
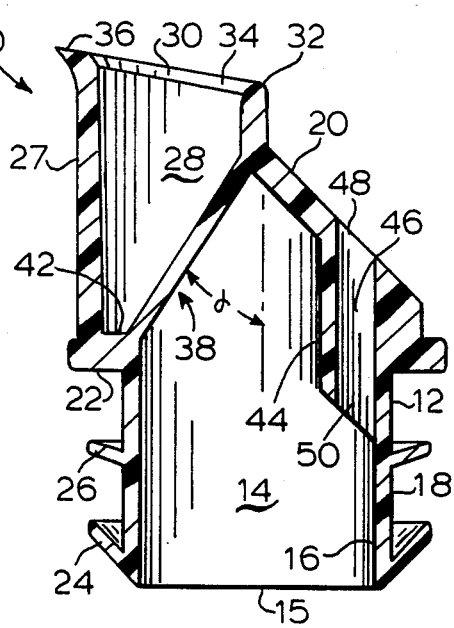
FIG. 2 is a cross-sectional view taken along line 2—2 of FIG. 1.
Figure 3:
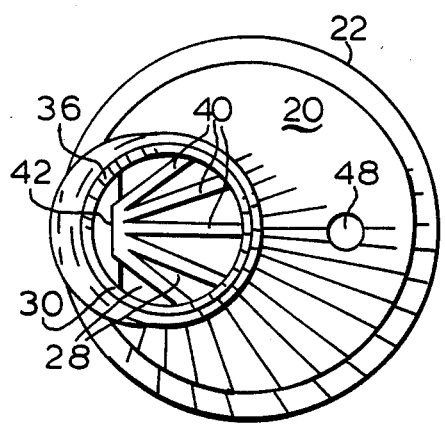
FIG. 3 is a top view of the present invention when viewed from line 3—3 of FIG. 2.
Figure 4:
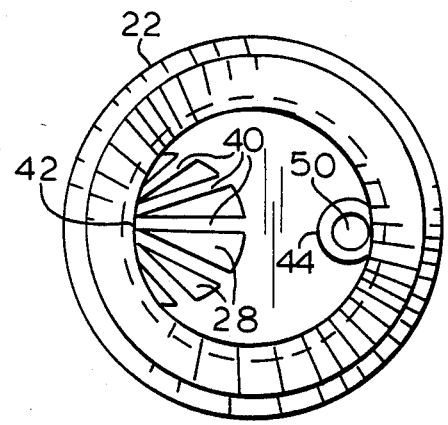
FIG. 4 is a bottom view of the present invention when viewed from line 4—4 of FIG. 2.

Referring now to FIGS. 1 to 4, and in particular to FIG. 2, there is illustrated a pouring spout of the present invention 10 formed of a suitable thermoplastic material such as polyethylene, polypropylene and the like. Pouring spout 10 is comprised of a generally cylindrically shaped side wall 12 forming a fluid channel 14. Fluid channel 14 terminates in an opening 15 at the bottom of the spout. Side wall 12 includes an inner surface 16 and an outer surface 18 partially enclosed at one end by a generally conically shaped top wall 20. Outer surface 18 of side wall 12 proximate to top wall 20 is formed with an outwardly extending disc shaped stop portion 22 which acts to limit insertion of the pouring spout into neck of the receiving container 52 as seen by briefly referring to FIG. 5.

Below stop portion 22 and formed outwardly from outer surface 18, there are formed lower and intermediate conically shaped resilient ring members 24 and 26, respectively, which function as stabilizing areas upon positioning the pouring spout within container 52, i.e., the rings are sized to permit insertion into containers of varying internal diameters resulting from manufacturing deviation in container production. Lower ring 24 additionally functions to prevent or minimize the flow of liquid between pouring spout 10 and the receiving container 52 with intermediate ring 26 functioning to prevent the pouring spout from popping out of the receiving container, as more fully hereinafter discussed.

Extending upwardly from one side of top wall 20 there is formed a cylindrically shaped wall member 27 forming a fluid channel 28 including an outlet orifice 30. The axis of channel 28 formed by the wall member 26 is preferably parallel to the axis of channel 14, but may be angled, if desired. It is preferred, however, that wall 27 be stepped away from, but lie substantially parallel to, side wall 12. A step 42 is thus formed which spaces wall 27 outwardly from the main cylindrical body. A top portion 32 of wall member 27 is preferably formed at an oblique angle to the axis of channel 28 to visually represent to the user a pouring direction. Top portion 32 is formed with an inner beveled surface 34 and an outwardly extending flared lip portion 36. The beveled surface facilitates the return of fluid within the pouring spout to the container, whereas lip portion 36 functions to break fluid flow and to minimize or prevent fluid drop flow along the outer surface of the wall member 27 of the pouring spout.

Between fluid channels 14 and 28 there is provided a screen 38 which is sufficiently porous to allow liquid to pass through but has enough interstices to entrap solids which may be present in the liquid. Screen 38 is preferably formed of a plurality of grate members 40 diverging outwardly in a flared or rayed configuration from step 42 at the intersection of side wall 12 with the wall member 27. Screen 38 is formed at an angle α to the axis of channel 14, with such angle preferably being greater than zero degrees but less than or equal to 90°. Generally, a smaller angle is preferred with an angle approaching 90° being somewhat less effective. It is noted that as angle α becomes smaller, the area between the grate members increases and that with the flared or rayed configuration such area will exponentially increase at increasing pouring angles for a given angle α. In other words, the area between the grate members proportionally increases for decreasing angle α, and, thus, the area for given angles of pouring is greater as the angle α becomes smaller. It will be understood that manufacturing capabilities and height limitations of the pouring spout defines practical limits to angle α. Such an exponential increase in area between grating members 40 as the pouring angle is increased results in the hereinbefore mentioned control flow of fluid from a container in which is inserted the pouring spout of the present invention.

Within channel 14 of the pouring spout there is formed by a portion of side wall 12 and a cylindrically shaped wall portion 44, a vent channel 46 including inner and outer orifices 48 and 50, respectively, functioning to permit pressure equalization between the fluid passageway in channel 14 and ambient atmosphere, thereby minimizing or preventing ebullition of the liquid normally associated with a pouring cap having a single fluid passageway. Vent channel 46 is preferably disposed as remotely as reasonably possible from the axis of fluid channel 28 to minimize bridging of the liquid or liquid leakage through vent channel 46. Additionally, the use of a channel instead of an orifice in the top wall 20 is preferred for like reasons with a longer vent channel as reasonably possible still further adding to controlled pouring with minimal ebullition. The wall portion constituting orifice 50 is preferably angularly formed with respect to a plane perpendicular to the axis of fluid channel 14 to facilitate air flow and tube venting. While desirable pouring could be effected such that the liquid being poured would not reach the vent channel, generally the liquid will reach the vent channel, and thus bubble formation is enhanced by the angular disposition of orifice 50 as distinguished from an orifice formed in the plane perpendicular to the axis of fluid channel 14.

Figure 5:
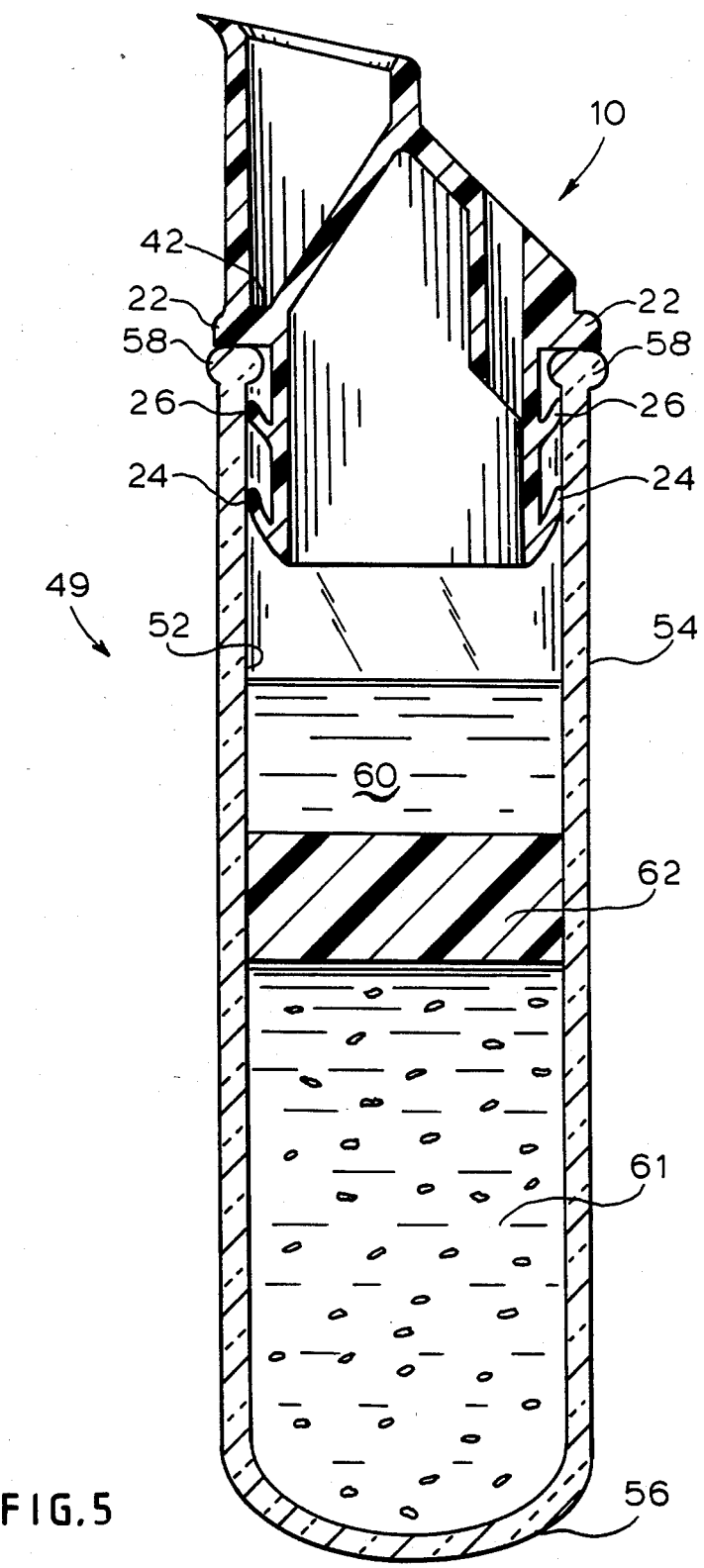
FIG. 5 is a cross-sectional view of the tubular container assembly.

Referring now to FIG. 5, there is illustrated a container assembly 49 comprised of pouring spout 10 substantially as described above, and a test tube 52 which preferably is adapted to contain serum, urine or other body fluids. Container or test tube 52 is comprised of a side wall 54, preferably of the cylindrical tubular form including a closed end 56 and an open glazed ring end portion 58. As clearly illustrated in FIG. 5, intermediate ring 26 of the pouring spout is formed such that the ring is caused to contact glazed ring 58 of the container thereby to keep the pouring spout from inadvertently popping out of the container.

In operation, the pouring spout 10 may be used with a serum separation device after a blood sample has been separated into a serum phase 60 and a heavy clotted blood phase 61 including fibrillar matter or generically fibrin (comprised of white insoluble fibrous proteins of varying lengths), such as disclosed in the aforementioned U.S. Pat. No. 3,852,194 to Zine, Jr. These phases are kept separated by an appropriate barrier material 62 such as described in the aforementioned patent. Therefore, only serum 60 will be decanted. One type of barrier material to be used is a thixotropic gel-like substance. While fibrin is generally concentrated in the heavier blood phase, some fibrin material is present in the serum phase (referred to as "latent fibrin") after coagulation and separation. The stopper of the separation device is replaced by the pouring spout 10 of the present invention. Upon tilting of the tube to a pouring angle approaching the horizontal, the lighter phase or serum 60 begins to move up the lower portion of the inner surface of container wall 54 to a point where the serum begins to pass through screen 38 and fall into fluid channel 28 and thence through orifice 30 and over lip portion 36. Step 42 allows the fluid to "drop away" from the screen into fluid channel 28. This provides faster flow of fluid away from the screen, and allows the screen to be cleared in the axial direction. As a result, the resistive effect of fluid already passed through the screen on fluid not yet passed through the screen is minimized. During initial use of the spout, this feature enhances the start of fluid flow. As a result of the presence and configuration of the screen 38, some of the latent fibrin, particularly the longer molecules, is caused to be trapped on grate members 40 of the screen thereby removing some of the latent fibrin from the serum. Further tilting causes the fluid level of serum 60 to rise on lower portion of the inner surface of container wall 54 thereby constantly enlarging the opened area exposed to fluid flow between grate members 40 to permit an ever increasing flow rate of serum.

As herein discussed, controlled flow is provided by the configuration of grate members 40, it being noted that a parallel grate configuration, while providing for increased fluid flow area at increasing pour angles, does not provide the exponential increase in flow area resulting from the illustrated configuration of the diverging grate members, although parallelly disposed grate members are feasible but with reduced effectiveness.

The configuration of the pouring spout of the present invention permits facile pouring of a liquid phase of sample from a container thereof into another vessel under conditions of control directional flow and under substantially dripless conditions.

The pouring spouts of the present invention, as hereinabove discussed, are readily formed of one-piece fabrication from conventionally available thermoplastic material, e.g., polyethylene, polypropylene and the like. The thermoplastic material should be inert to the liquid sample, e.g., blood, and be compatible with liquid flow.

In use for the decantation by pouring of blood serum, the sizing of the filter grates or channels is selected to effectively remove fibrin from the blood serum deleterious to further processing while minimizing resistance to fluid flow, it being understood that such sizing may be varied for other types of duty to which the pouring spout may be placed in respect to other solid-liquid phase systems.

While the invention has been described in connection with an exemplary embodiment thereof, it will be understood that many modifications will be apparent to those of ordinary skill in the art and that this application is intended to cover any adaptations or variations thereof. Therefore, it is manifestly intended that this invention be only limited by the claims and the equivalents thereof.

What is claimed is:

1. A pouring spout for use with a container for the withdrawal of a liquid from the container under conditions of controlled flow, which comprises:
 a body side wall enclosed at one end by a top wall and defining a first fluid channel;
 a spout member extending outwardly from said top wall and defining a second fluid channel having a fluid outlet orifice, said channels being in fluid communication with each other and defining a fluid passageway for said liquid;
 screen means angularly disposed in said fluid passageway for removal of solids from said liquid; and
 vent means for providing pressure equalization between said passageway and ambient atmosphere.

2. The pouring spout as defined in claim 1 wherein said top wall is conically shaped upwardly from said body side wall.

3. The pouring spout as defined in claim 2 wherein said screen means is disposed between said first fluid channel and said second fluid channel.

4. The pouring spout as defined in claim 3 wherein said screen means is comprised of diverging grate members defining increasing open areas at increasing pouring angles.

5. The pouring spout as defined in claim 4 wherein said grate members define exponentially increasing open areas.

6. The pouring spout as defined in claim 3 wherein said screen means is disposed at an angle of from greater than zero degrees to 90° to the axis of said first fluid channel.

7. The pouring spout as defined in claim 1 wherein the axis of said second fluid channel is off-set from said axis of said first fluid channel.

8. The pouring spout as defined in claim 7 wherein said spout member has an outside wall surface stepped outwardly from said body side wall.

9. The pouring spout as defined in claim 1 wherein said vent means is a vent channel having an outer orifice through said top wall and an inner orifice in said first fluid channel.

10. The pouring spout as defined in claim 9 wherein said inner orifice is obliquely formed with respect to said body side wall.

11. The pouring spout as defined in claim 1 wherein stabilizing ring means are formed about said body side wall for positioning said pouring spout within said container.

12. The pouring spout as defined in claim 11 wherein said stabilizing ring means is comprised of a lower stabilizing ring and intermediate stabilizing ring, said intermediate stabilizing ring being disposed for contact with a glazed portion of said container.

13. The pouring spout as defined in claim 1 wherein said spout member is formed with a pouring lip.

14. A container assembly which comprises:
 a container having a side wall and enclosed by an end wall and formed with an opening at the other end thereof; and
 a pouring spout disposed within the opening in said container, said pouring spout being comprised of a cylindrically shaped body side wall, a spout member, a screen means and a vent means, said cylindrically shaped body side wall enclosed at one end by a top wall and defining a first fluid channel, said spout member extending outwardly from said top wall and defining a second fluid channel having a fluid outlet orifice, said fluid channels being in fluid communication with each other and defining a fluid passageway for said liquid, said screen means angularly disposed in said fluid passageway for removal of solids from said liquid, said vent means providing for pressure equalization between said passageway and ambient atmosphere.

15. The container assembly as defined in claim 14 wherein said container is provided with a thixotropic gel-like material.

16. The container assembly as defined in claim 14 wherein said open end includes a glazed ring element.

17. The container assembly as defined in claim 16 wherein said body side wall of said pouring spout is formed with a stabilizing ring at a point for operative association with said glazed ring element of said container.

* * * * *